United States Patent
Ward et al.

(10) Patent No.: US 6,425,430 B1
(45) Date of Patent: *Jul. 30, 2002

(54) APPARATUS FOR MAKING COMPOSITE SHEET

(75) Inventors: Robert Roch Ward, Chesterfield, VA (US); Joshua Benin, Newark; Cathy Jane Hamilton, Wilmington, both of DE (US); Leslie C. Talo, Neenah, WI (US)

(73) Assignee: E. I. du Pont de Nemours & Company, Wilmington, DE (US)

( * ) Notice: Subject to any disclaimer, the term of this patent is extended or adjusted under 35 U.S.C. 154(b) by 105 days.

This patent is subject to a terminal disclaimer.

(21) Appl. No.: 09/610,131

(22) Filed: Jul. 5, 2000

Related U.S. Application Data

(60) Division of application No. 09/169,811, filed on Feb. 26, 1998, now Pat. No. 6,179,946, which is a continuation-in-part of application No. 08/695,263, filed on Aug. 9, 1996, now abandoned, which is a continuation-in-part of application No. 08/510,994, filed on Aug. 3, 1995, now abandoned.

(51) Int. Cl.$^7$ ............................................. B32B 31/06
(52) U.S. Cl. ...................... 156/440; 156/439; 156/447
(58) Field of Search .................................. 156/176, 177, 156/179, 434, 436, 439, 440, 229, 292, 447; 242/43, 158.3, 158.5

(56) References Cited

U.S. PATENT DOCUMENTS

| | | | |
|---|---|---|---|
| 2,812,797 | A | 11/1957 | Estee et al. |
| 2,962,080 | A | 11/1960 | Hirsch |
| 3,086,722 | A | 4/1963 | Altice et al. |
| 3,607,565 | A | 9/1971 | Eaton |
| 3,675,863 | A | 7/1972 | Akers et al. |
| 3,878,591 | A | 4/1975 | Jense |
| 4,080,232 | A | 3/1978 | Friedrich |
| 4,600,468 | A | 7/1986 | Kelly et al. |
| 5,000,806 | A | 3/1991 | Merkatoris et al. |
| 5,221,390 | A | 6/1993 | Persson et al. |
| 5,296,080 | A | 3/1994 | Merkatoris et al. |

*Primary Examiner*—Sam Chuan Yao

(57) ABSTRACT

A process and an apparatus for high speed manufacture of a composite sheet material, which includes a cylindrical cam-driven strand-traverse guide that can loop strands around pins projecting from a pair of advancing pin conveyors which can transfer the strands to the surface of a moving sheet, are provided. When the strands are elastic, the elastic composite sheet material made by this process and apparatus are useful in elastic components of disposable diapers, adult incontinence articles and other garments.

5 Claims, 11 Drawing Sheets

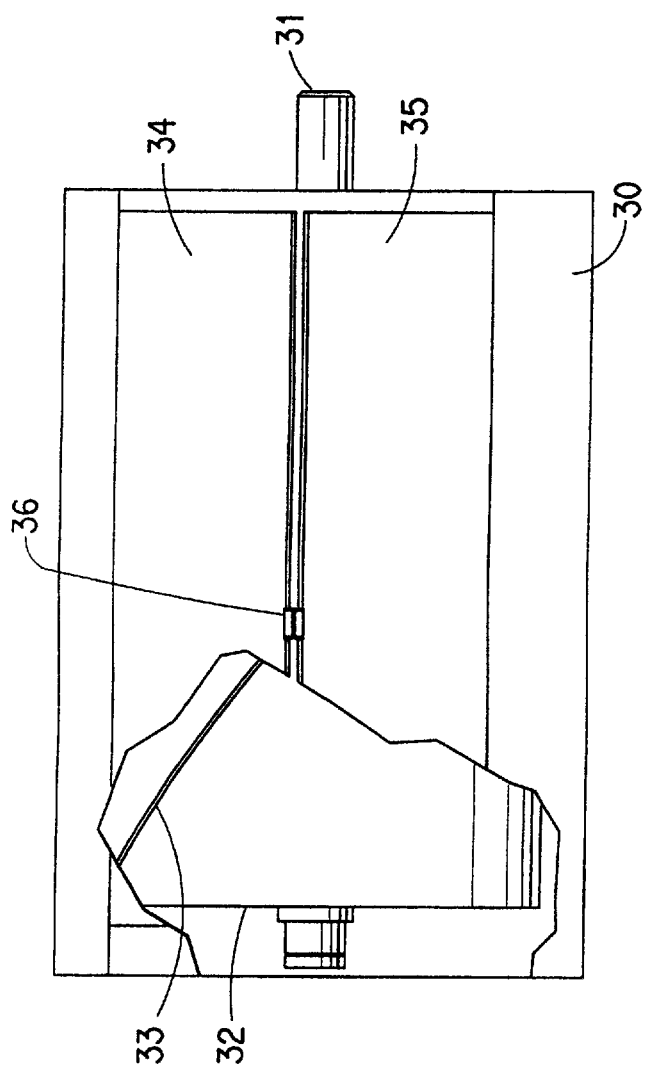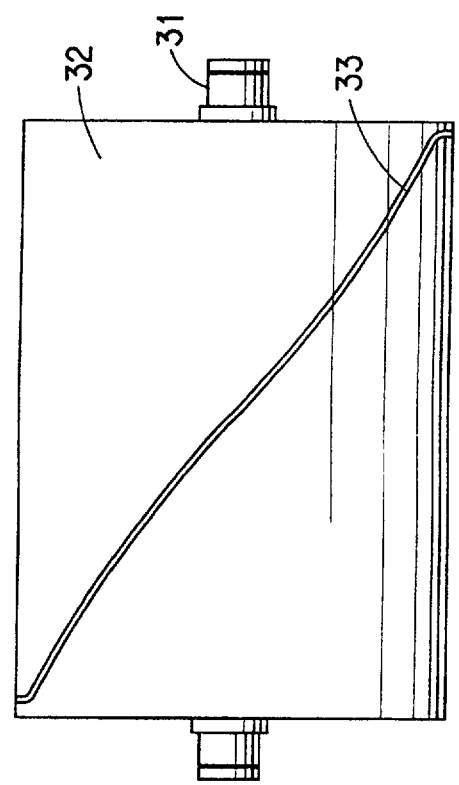

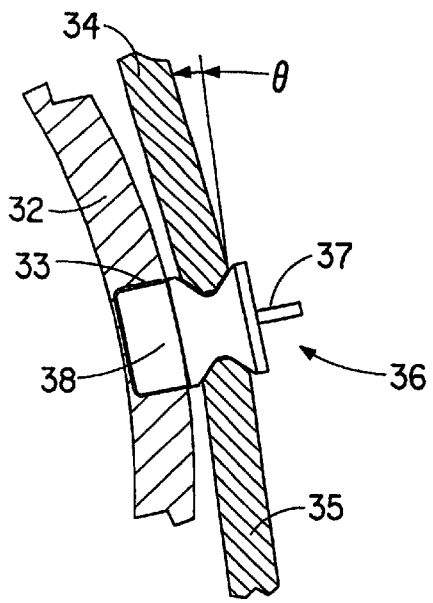 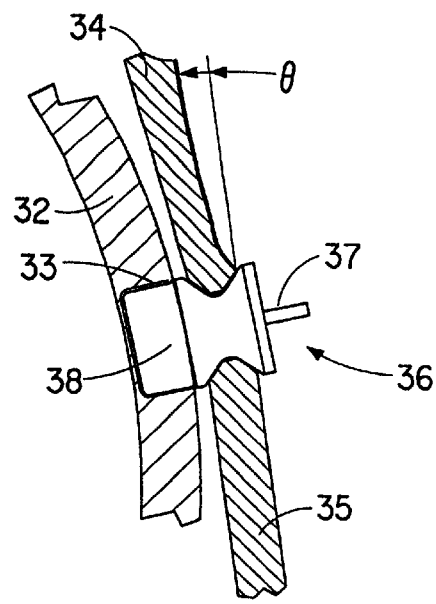
FIG.11a   FIG.11b
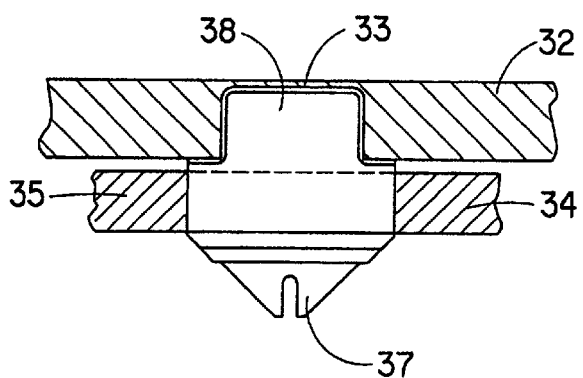
FIG.12
FIG.13

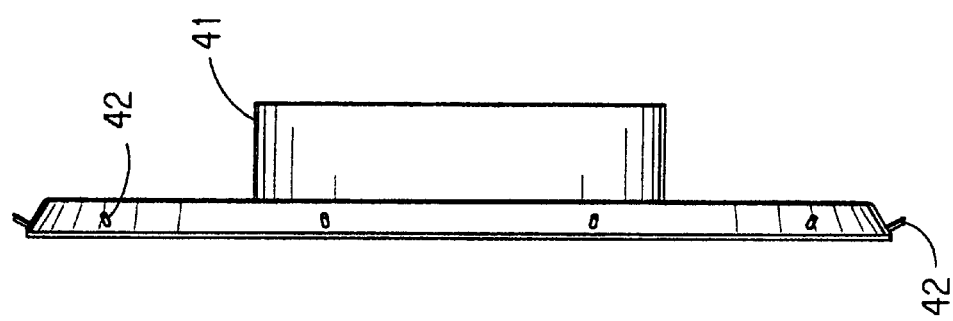
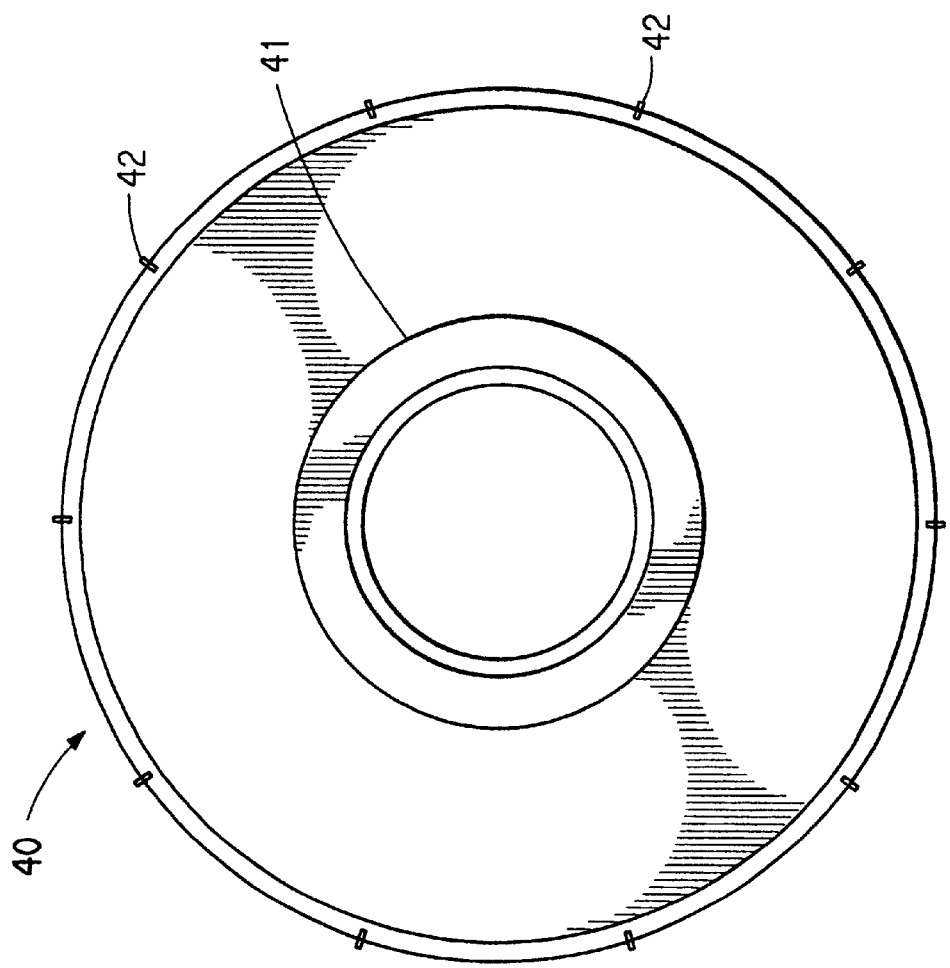

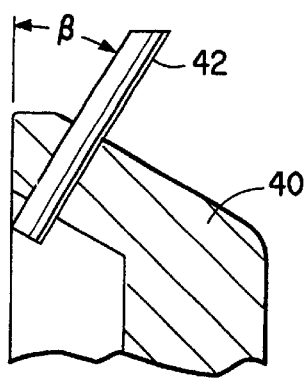
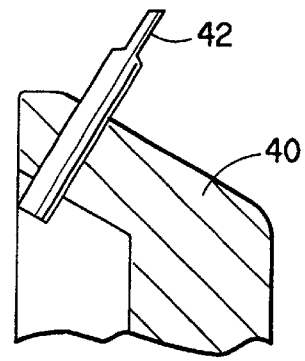
FIG. 15a FIG. 15b
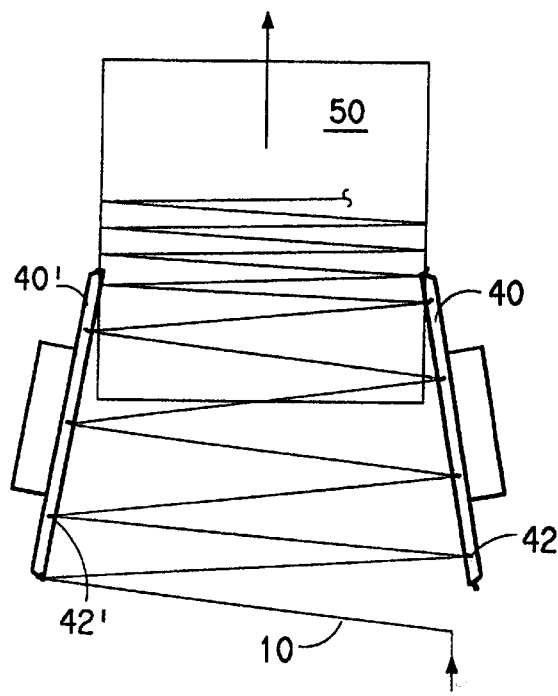
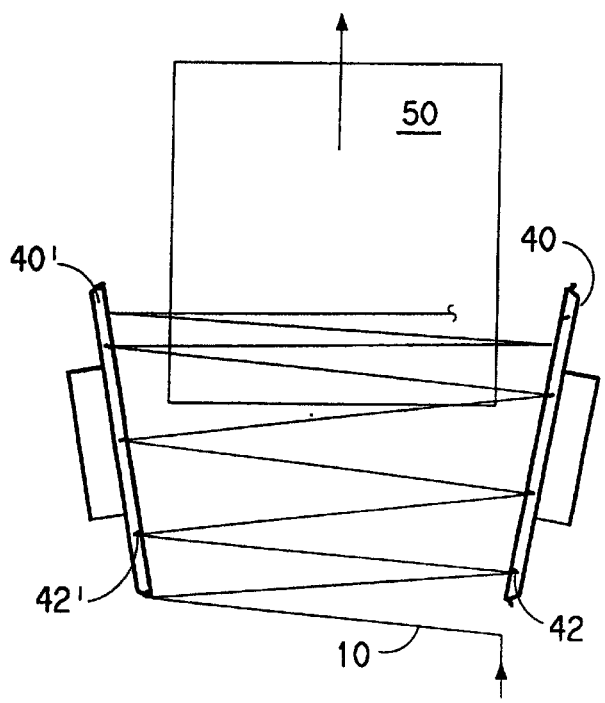
FIG. 16a FIG. 16b

APPARATUS FOR MAKING COMPOSITE SHEET

CROSS-REFERENCE TO RELATED APPLICATION

This is a division of application Ser. No. 09/169,811 filed Feb. 26, 1998, now U.S. Pat. No. 6,179,946 B1 which is a continuation-in-part of U.S. application Ser. No. 08/695,263, filed Aug. 9, 1996 now abandoned which was a continuation-in-part of U.S. application Ser. No. 08/510,994, filed Aug. 3, 1995, now abandoned.

BACKGROUND OF THE INVENTION

1. Field of the Invention

This invention relates to a process and apparatus for making a composite sheet material wherein a strand is attached transversely to a moving sheet. More particularly, the invention concerns a high speed process and apparatus in which a strand, carried by a reciprocating strand traverse guide that is driven by a rotating cylindrical cam, is looped around pins projecting from a pair of pin conveyors which then transfer the strand from the pins to the surface of the moving sheet.

2. Description of Background Art

Known processes for producing a continuous, cross-direction laydown of strands onto a moving sheet are complex, slow and often unsuitable for use with elastic strands. Typical processes for production of cross-direction elastic features (e.g., a waistband) in a disposable diaper, for example, use the much easier machine-direction strand laydown, followed by a complex, slow, cut-and-turn procedure to orient the strands in the cross-direction. Techniques that produce direct strand laydown in the cross-direction are slow. An example of this is the rotating arm technique, similar to a braiding process. Laydown rates are too slow to be attractive. Increasing the strand pitch will increase rates but also introduces an undesirable machine-direction elasticity. Oscillating or swinging arm procedures have the same limitations. Attempts to increase rate by using simultaneous laydown of multiple strands must incorporate steeper laydown angles and/or machine-direction displacement at intervals. These alterations reduce the effectiveness of the elastic strand and introduce substantial machine-direction elasticity and attendant strand waste.

Processes and apparatus are known in which a continuous filament or strand is laid across and attached to the surface of moving sheet. For example, Estee et al, U.S. Pat. No. 2,812,797, discloses an apparatus for making a laminated fabric. In the apparatus, a sheet is continuously advanced between two endless belts that travel in unison and in the same direction as the sheet. One belt is located at each edge of the sheet and each belt has a series of pins projecting from its surface. A swinging frame traverses a plurality of continuous filaments back and forth across the sheet. At each reversal of the traverse, each filament from the frame is looped around a corresponding pin of the belt. Adhesive is applied to the sheet and the filaments. Then, the filaments are disengaged from the pins and adhered to the sheet surface to form an assembly of filaments and sheet. A cover sheet is placed atop the assembly and passed with the filament/sheet assembly between calender rolls to produce the laminated fabric. In another method, disclosed by Hirsch, U.S. Pat. No. 2,962,080, an endless chain mechanism equipped with spaced apart pins, or a swinging lever mechanism equipped with a thread guide, traverses a thread across a sheet that is moving perpendicularly to the path of the traverse. Outside each edge of the sheet is a moving endless chain, equipped with a plurality of spaced apart pins. The thread from the traversing mechanism, at one end of each traverse path, deposits the thread around a pin on the chain at one edge of the sheet and then at the other end of the traverse path deposits thread on a pin of the chain on the other edge of the sheet. Although this method is suitable for use with non-elastic thread, the method is slow and unsuited for use with elastic thread.

Other methods for traversing filaments or strands across a moving surface to form reinforced sheets, scrims or nets also are known. For example, a reciprocating conveyor is disclosed by Friedrich, U.S. Pat. No. 4,080,232, flaying reads on the outer surface of a rotating cylinder that has barbs projection both edges of the cylindrical surface to restrain the threads and form an open mesh net-like structure. Kelly et al, U.S. Pat. No. 4,600,468, also discloses a method for laying out biased arrays of parallel yarns on conveyors equipped with needles to restrain the yarns and adhesively bonding the arrays together to form a bias-laid nonwoven fabric. A rotating arm is disclosed by Persson et al, U.S. Pat. No. 5,221,390, for positioning conventional or elastic threads on "dogged elements" (e.g., pins or studs) projecting from a pair of belts located at the edges of a conveyor path. Merkatoris et al, U.S. Pat. No. 5,000,806, discloses a method and apparatus for applying elastic strand to a disposable diaper by means of canted, spindle-equipped wheels for engaging the elastic strand, moving the strand into a sinuous configuration, stretching the strand and thereafter applying the strand transversely to an advancing component of the diaper.

Each of the above-described methods and apparatuses are complex and do not attain high speeds which are desired for efficient and economical attachment of strand in a transverse direction to a moving substrate. Further, some of these methods are not suited for handling elastic strands.

Though not concerned with the problems associated with attaching strand to moving sheets, various mechanisms for traversing strand across a path are known. For example, Altice et al, U.S. Pat. No. 3,086,722, and Akers et al, U.S. Pat. No. 3,675,863, disclose yarn traversing guides driven by rotating cylindrical cams for high speed winding of yarn packages, such as bobbins, cakes and the like.

SUMMARY OF THE INVENTION

The process of the present invention for making a composite sheet material, in which a sheet substrate is advanced in a machine direction and a continuous strand is attached to the surface of the sheet transversely to the machine direction (i.e., in a generally cross-machine direction) comprises the following steps:

advancing in a longitudinal direction a sheet substrate, a first conveyor and second conveyor, the sheet having two lateral edges and an upper and a lower surface and each conveyor having a plurality of spaced apart pins extending therefrom in a direction generally perpendicular to the movement of the conveyor;

supplying a strand with a controlled degree of elongation to an oscillating barrel cam and thread guide device that reciprocates the strand to and from across a traverse path, the traverse path being generally transverse to the longitudinal direction of the advancing sheet substrate, wherein the pattern of the thread guide is controlled by the barrel cam design so as to allow sufficient stroke width and/or reversal dwell time to cause the strand to wrap around the pin on the advancing conveyor without striking the pin or the conveyor;

advancing the conveyors to move the pins through a semicircular path that intersects the traverse path of the strand, thereby causing the strand to loop alternately around a pin on the first conveyor and then on a pin of the second conveyor at each end of the traverse path to form a cross-directional continuous strand array carried by the pins;

applying an adhesive to the strand array and/or the advancing sheet substrate;

transferring the strand array from the pins to the upper surface of the advancing sheet substrate while restraining each edge of the strand array in position on the advancing sheet substrate until the applied adhesive is set to form a strand-sheet assembly;

optionally attaching a cover sheet atop the strand-sheet assembly; and forwarding the resultant composite sheet material to a windup or further processing.

By generally "cross-machine direction" is meant that cross strands can be laid down on the moving sheet substrate at angles of 45–90° to the machine direction.

The invention also provides an apparatus for performing the above-described process and a garment having an elastic component made with an elastic composite sheet material of the process.

BRIEF DESCRIPTION OF THE DRAWINGS

The invention will be better understood by reference to the attached drawings in which:

FIG. 8 is a partial cut-away front view of housing 30 showing cylindrical cam 32, strand guide 36, positioned between upper and lower traverse guide rails 34 and 35 respectively;

FIG. 9 is a front view of cylindrical cam 32 having groove 33 into which the cam follower portion of the strand guide is fitted and slides;

FIGS. 11a and 11b each depict in a detailed side-view cross-section, similar to that of FIG. 6, two geometries for guide rails 34 and 35;

FIG. 12 is a top view detailed cross-section of cam follower 38 in groove 33 of cylindrical cam 32 and of slotted tip 37 of strand traverse guide 36;

FIG. 13 depicts another embodiment the slotted tip 37 of strand guide 36;

FIGS. 14a and 14b are respectively a front view and a side view of pin-conveyor wheel 40;

FIGS. 15a and 15b illustrate in detailed side view two embodiments of pins 42 mounted on a pin-conveyor wheel 40;

FIGS. 16a and 16b respectively illustrate in top view two embodiments of pin-conveyor wheels 40 and 40' canted inwardly or outwardly in relation to sheet 12 to be advanced on sheet support drum 50.

DETAILED DESCRIPTION OF THE INVENTION

Figure 1:
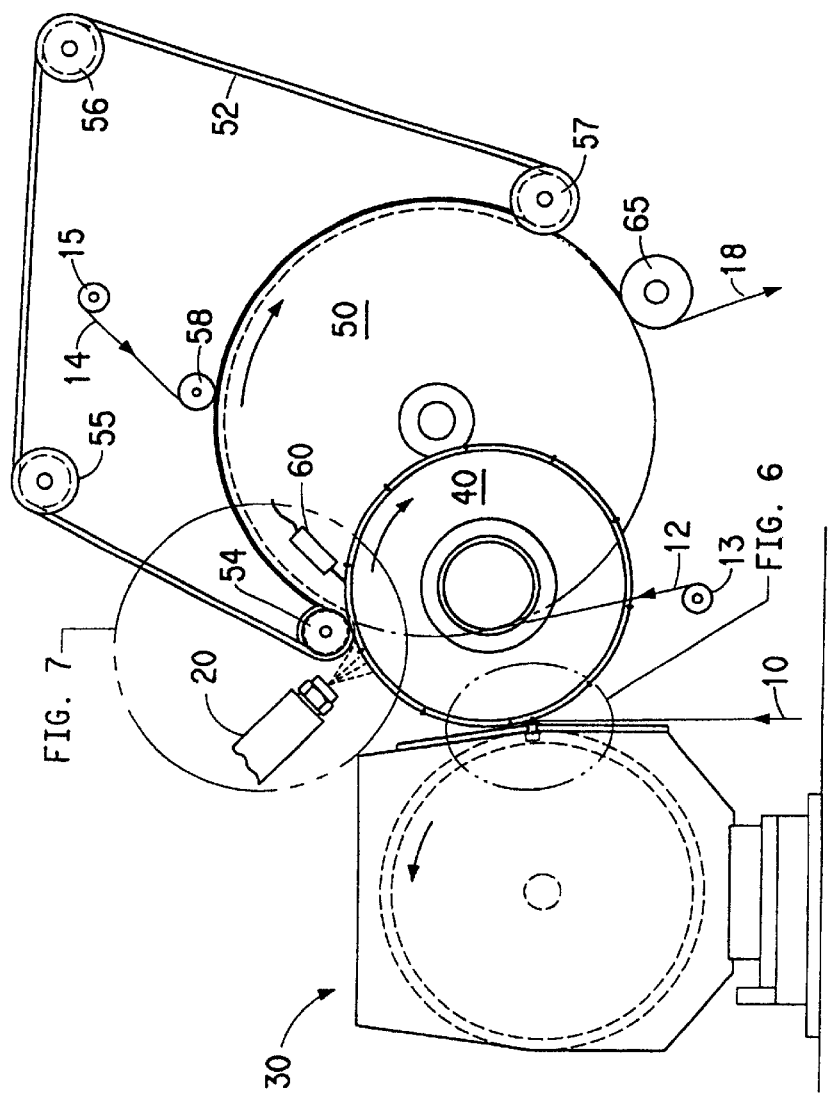
FIG. 1 is a side view schematic diagram of an apparatus for making composite sheet material according to the invention showing relative locations of housing 30 which holds a cylindrical cam and a strand traverse guide, pin-conveyor wheel 40 and sheet support drum 50.

Preferred embodiments of the process and apparatus for making composite sheets according to the invention will now be described with reference to the accompanying Figures.

The apparatus comprises three main components; namely, a cam-driven guide housing 30, pin conveyors 40, 40' and a sheet forwarding and supporting unit 50. Housing 30 contains cylindrical cam 32 that drives strand traverse guide 36 to cause strand 10 to be looped around pins 42,42' of a pair of pin conveyors 40, 40' to form a strand array 16. A sheet 12 is advanced on sheet support unit 50 and assembled with strand array 16 and optionally with a cover sheet 14 to form composite sheet material 18, which then can be wound up or forwarded to further processing operations.

Figures 4, 5:
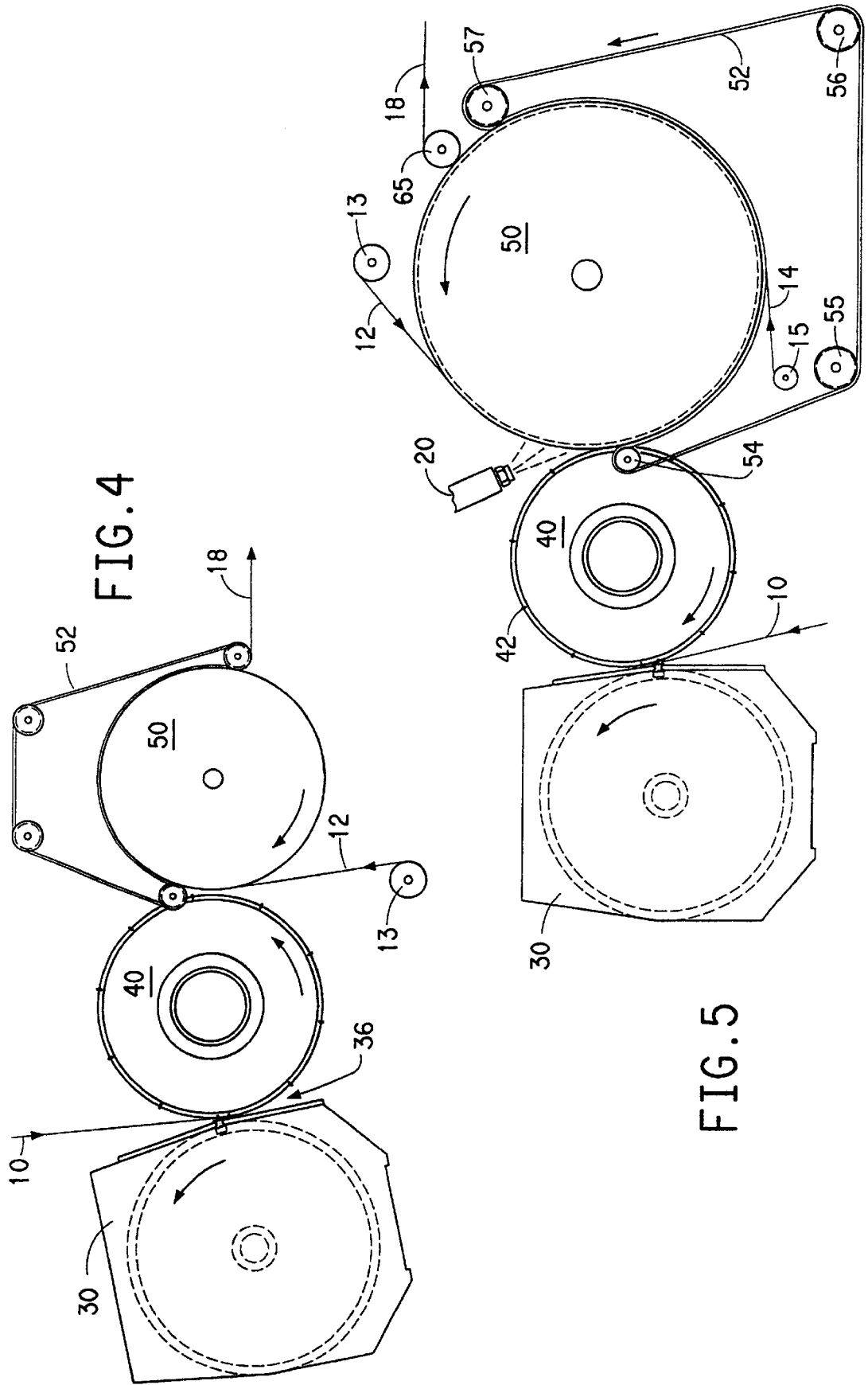
FIG. 4 is a side view of another suitable arrangement of housing 30, pin-conveyor wheel 40, sheet support drum 50 and restraining belt 52.
FIG. 5 is a side view of still another arrangement of housing 30, pin-conveyor wheel 40, sheet support drum 50 and restraining belt 52 for an apparatus of the invention for making composite sheet material 18 with a cover sheet 14.

In accordance with the process of the invention, strand 10 is supplied to strand traverse guide 36 from below the guide as shown in FIGS. 1 and 5, or from above the guide as shown in FIG. 4. When spandex is employed as the strand to be incorporated into the composite sheet material, a simple feed path is preferred for the strand from the supply to the traverse guide with as few idler rolls as practicable. One idler roll can suffice to feed the strand from a supply package (e.g., a bobbin or a cake) to the traverse guide. Such a feed path minimizes the amount of friction and tension to which the strand is subjected and permits smoother, more uniform feeding of strand to the apparatus. Typically, the spandex is supplied to the apparatus with an extension of 10 to 400% beyond the relaxed length of the spandex via the use of a positive feed unwinder. By controlling the speed of the unwinder relative to the rate of strand lacing onto the pins of the conveyor, a controlled degree of strand elongation can be achieved. By synchronizing the speed ratio, the strand elongation can be held constant over the entire speed range of the process.

Typically, the reciprocating traverse guide traverses the strand at a rate of 250–3000 to-and-from cycles/min, has a stroke (i.e., one-half of a to-and-from cycle) that is at least 15 centimeters long, preferably at least 20 cm; although a stroke length of 5 cm is acceptable. Preferably, the strand is an elastic strand, most preferably a spandex. The elastic strand is elongated in the range of 10 to 400% beyond its original relaxed length while being supplied to the strand traverse guide and/or while being restrained in the strand array.

The laydown angle of the strand on the conveyor pins (i.e., the conveyor pin spacing), can be chosen to allow ease of laydown. Through differential control of the conveyor speed and the speed of the moving sheet substrate, final strand spacing can be altered to produce different composite constructions with the same apparatus. Final strand spacings of from 1 strand per machine direction inch to 20 strands per machine direction inch can be achieved. The process tolerates a wide variety of strand sizes, can accommodate a wide range of strand elongations, can achieve a wide variety of final thread spacings and can be used with a wide range of substrates to allow production of a multitude of different composites.

Figure 6:
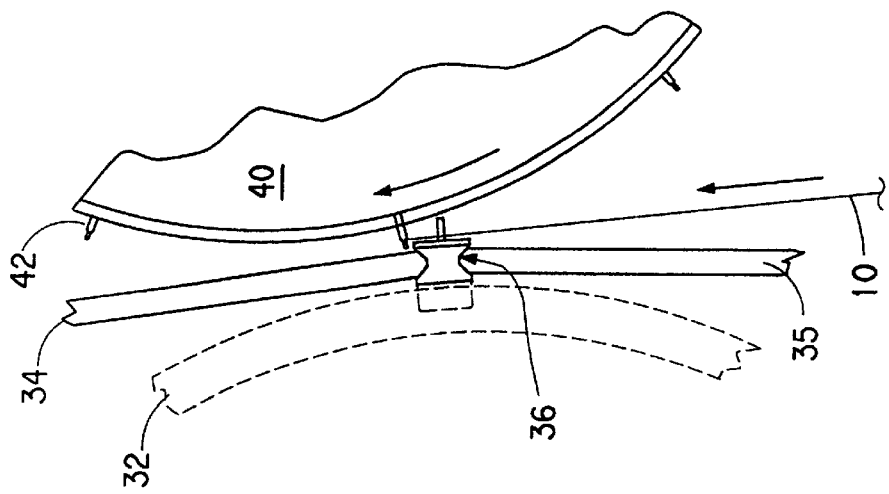
FIGS. 6 and 7 are each an enlarged side view of an area enclosed by dashed lines in FIG. 1.
Figure 7:
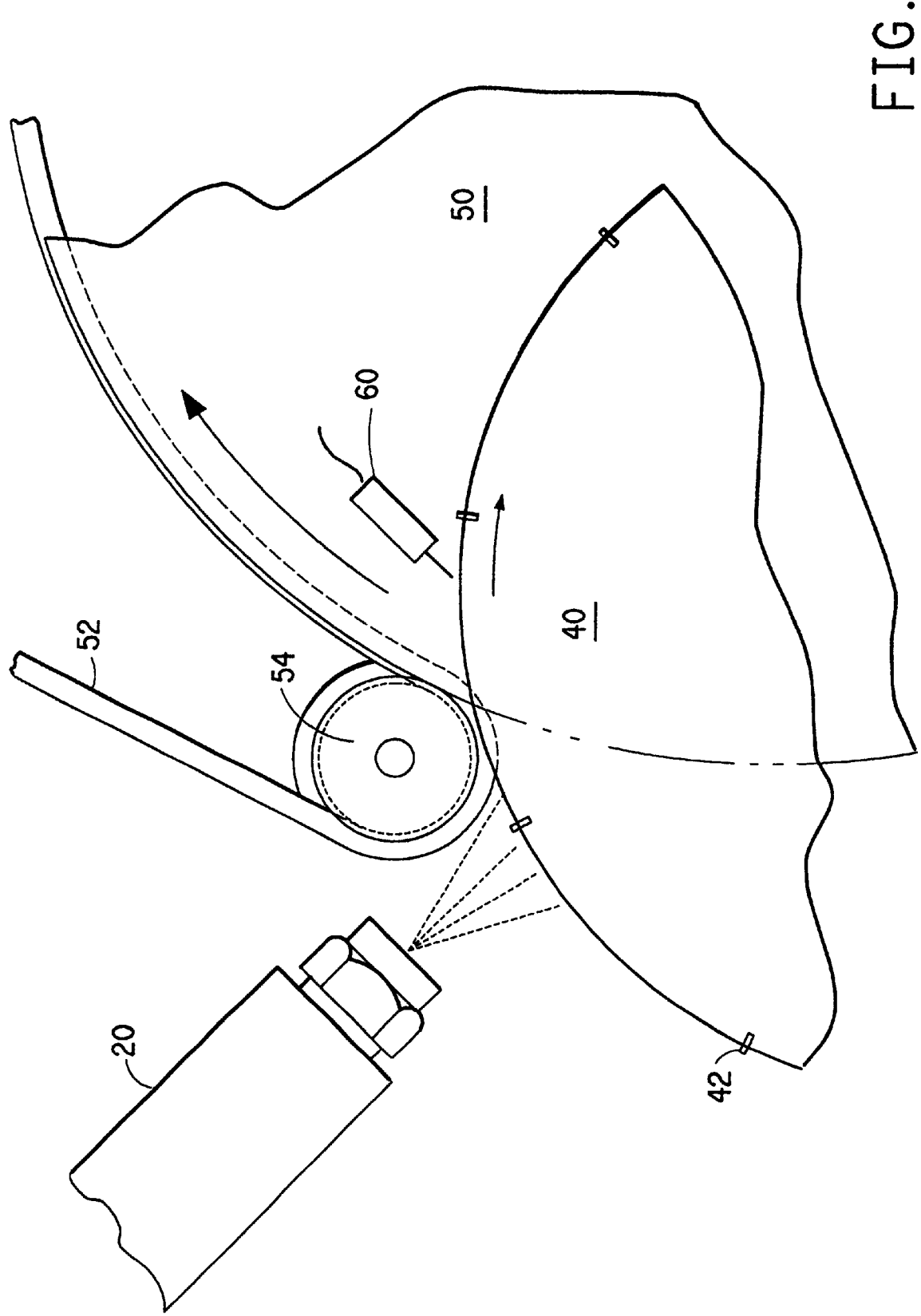

As illustrated in FIGS. 6, 8, 11a, 11b and 12, strand traverse guide 36 has cam follower portion 38 that is mounted in groove 33 of rotating cylindrical cam 32. Strand guide 36 rides between upper and lower rails 34 and 35. As cylindrical cam 32 is rotated, strand traverse guide 36 traverses a path that is perpendicular to and intersected by the paths of pins 42, 42' carried by two spaced-apart pin conveyors. In the figures, the pin conveyors are illustrated as pin-conveyor wheels 40, 40'. Each wheel has a plurality of pins 42, or 42' projecting from its circumference. As wheels 40, 40' are rotated, strand 10 is looped by strand traverse guide 36 around each pin, first on a pin of one pin-conveyor wheel and then on a pin of the other pin-conveyor wheel, to form strand array 16. For each cycle of the traverse guide to and from, each pin-conveyor wheel is advanced by the angular distance between successive pins. Strand array 16 is then carried by the rotating pin-conveyor wheels into contact with advancing sheet 12 as the sheet is fed from supply roll 13 onto and advanced by a sheet support surface, illustrated in the figure. as rotating drum 50. A short distance upstream of the location where strand array 16 contacts advancing sheet 12 an adhesive, preferably a melt adhesive, is applied to the strand array and/or the sheet by spraying, dripping, or other means. In FIGS. 1, 5 and 7, the adhesive is applied through adhesive spray applicator 20. The strand array is carried by continued rotation of the pin-conveyor wheels into one or more nips located near each edge of the strand array. The nips are formed by restraining belts 52, 52', preferably V-belts, and the circumferential surface of rotating drum 50. Then, strand array 16 is removed from the pins and held by the restraining belts atop advancing sheet 12 on the drum surface.

Strand removal can be accomplished by any of several methods. The strand can simply be allowed to break as the elongation of the unrestrained end-loop exceeds the break elongation of the strand via the continued separating movement of the pin conveyor and the assembly drum. Alternatively, the strand can be deliberately released from the pin at a prescribed point after the strand has been sufficiently restrained by the belts via a retracting or folding pin movement.

Optionally, a cover sheet 14 fed from supply roll 15 can be applied atop the just-formed strand array/sheet assembly. By setting the traverse speed and the pin spacing on each pin conveyor, and then adjusting the relative speeds of the pin conveyors and the sheet-advancing support, the number of transverse strands per unit length of composite sheet material produced can be varied as desired. As the assembled sheet substrate 12, strand array 16 and optional cover sheet 14 are advanced, the adhesive becomes set and composite sheet material 18 is completed. Then, the composite sheet can be wound up or forwarded to further processing operations.

When the strand employed in the process or apparatus of the invention is an elastic strand (e.g., spandex), the resultant composite sheet material 18 can be cut in an optional subsequent step substantially parallel to the direction of the transverse strands to form elastic tapes or swatches. Then, the elastic tapes or swatches can be attached as elastic waistbands, side panels, closure tapes, frontal tapes, back panels and leg bands to disposable diapers and adult incontinence articles. Composite sheet material 18 formed by the process of the invention with strand that is not elastic can be useful as strand-reinforced fabric, film, laminate, and the like. In such uses, strand 10 preferably is made of high tenacity fibers or filaments of polymers such as nylon, aramid, polyolefm, or polyester, or of glass or the like.

As used herein the term "strand" includes any monofilament, multifilament. or staple yarn or thread. The strand can be of any decitex suitable for the application for which the resulting composite sheet material is intended. The strand can be made of synthetic or natural fibers. For elastic composites, the strand can be of natural or synthetic materials such as rubber, spandex or other elastomeric material. The term "spandex" has its usual generic meaning; namely, fiber made from a long chain synthetic polymer that comprises at least 85% by weight segmented polyurethane. Preferably, the spandex is employed with no lubricating finish on its surface so that better adhesion can be obtained between the spandex and the sheets.

Sheets suitable for use in the invention as advancing sheet substrate 12 include film, paper, woven fabric, knit fabric or non-woven fabric. The fabrics can be of natural or synthetic fibers such as cotton, wool, polyester, nylon, polypropylene, polyethylene, or the like. The films can be of polyethylene, polyester, polyfluorocarbons, polyimide, polypropylene, or the like.

The resultant composite sheet material when formed with non-elastic strand is reinforced in the transverse direction of the composite sheet material. Composite sheet that was formed with elastic strand is elastic in the cross (transverse) direction and displays a number of desirable features. Due to the use of very high, almost perpendicular (i.e., extremely cross-directional) strand laydown, the composite exhibits a high degree of asymmetry. The composite, while elastic in the cross direction, exhibits substantially no elasticity in the machine direction. This is a very desirable combination of properties. Because of the high strand laydown rates afforded by the barrel cam design, dense (i.e., high strands/machine direction inch) strand patterns can be achieved without excessive loss of production rate, allowing composites displaying desirable, uniform elastic behavior to be created. By independently varying strand size, elongation and final laydown pattern, desirable combinations of speed, degree of elasticity and composite aesthetics can be achieved. Such elasticized composite sheet materials can be cut into tapes or swatches of suitable dimensions and fed directly to the elastic swatch applicator of a garment-making machine to form the desired elastic component in the garment.

Composite sheet materials 18 made by use of the process and apparatus of the invention typically have desirable resistances to impact, puncture and tear. Properties of the composite sheet can be further enhanced by processing the composite sheet material through the apparatus again one or more times. Uses for composite sheet material produced by the invention include tarpaulins, cargo curtains, bags, inflatable structures, hospital gowns, disposable coveralls, and the like. In some uses, elastomeric and reinforcing strands can be used advantageously together.

Various embodiments of the apparatus of the invention will now be described in further detail.

Cam/traverse-guide housing 30 encloses rotatable cylindrical cam 32. Housing 30 also supports upper and lower guide rails 34, 35, between which strand traverse guide 36 is mounted. Housing 30 also prevents lubricating oil used on the cam from spraying into the work area. A 30-weight oil is suitable for lubricating the cam. FIG. 8 is a front view of housing 30, with a portion cut away to show cylindrical cam 32 within. Cylindrical cam 32 has groove 33 cut into its surface. The cylindrical cam is rotated by means not shown through cam shaft 31. As shown by FIGS. 11a, 11b and 12, strand traverse guide 36 comprises a tip 37 for holding the strand and a base 38 which acts as a cam-follower. The base or cam-follower portion 38 of strand traverse guide 36 is seated in cam groove 33 and slides through the groove path as cylindrical cam 32 is rotated. Rotation of grooved cylindrical cam 32 causes strand traverse guide 36 to slide to and from between the straight edges of upper and lower guide rails 34 and 35. FIG. 9 is a front view detail of the cylindrical cam 32 with groove 33 in which the stand traverse guide cam follower base 38 is to be seated. An access notch, not shown, can be provided in one of the guide rails for convenient installation of the strand guide in the cam groove and between the guide rails. A lead-in channel, not shown, connected to the groove in the circumferential surface of the cam, in a position that can be aligned with the access notch in the guide rail, permits convenient seating and removal of the strand guide.

Figure 10A:
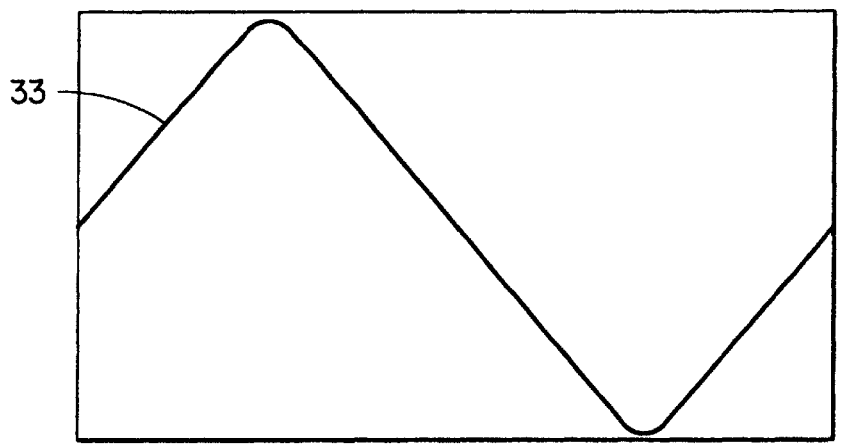
FIGS. 10a, b and c illustrate planar developments of three profiles of the groove 33 of cylindrical cam 32.
Figure 10B:
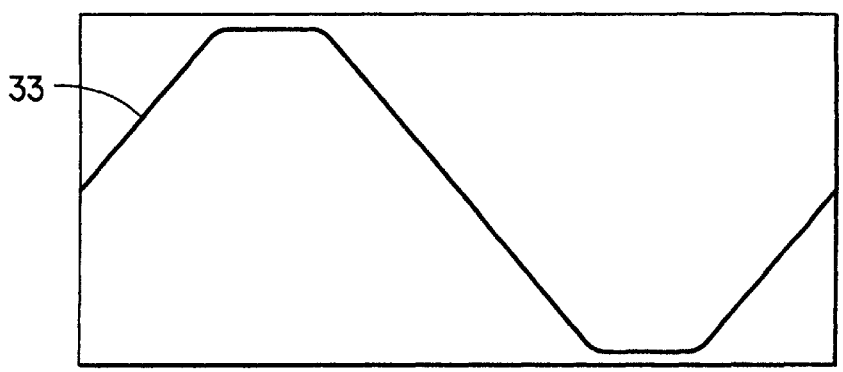
Figure 10C:
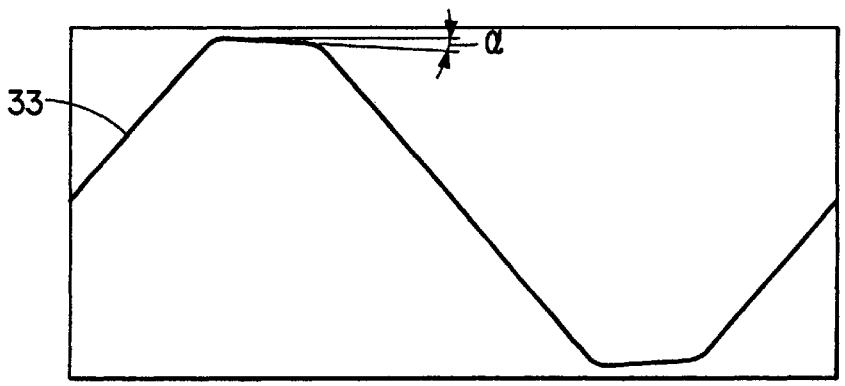

FIGS. 10a, 10b and 10c show three developed surfaces or "profiles" of cams for use in the apparatus of the invention. Each profile represents the complete surface of a cylindrical cam laid out in a plane. The curve represents groove 33 of cylindrical cam 32. In operation, the cam follower of the strand traverse guide follows the groove path. The profile represents one rotation of the cam and results in one to and from traverse of the strand traverse guide. Alternatively, suitable cams can have more than one rotation of the cam resulting in one to-and-from traverse of the strand traverse guide. In following the groove of the cam profile shown in FIG. 10a, the strand guide reverses direction immediately upon reaching the extreme end of its traverse. This cam is very similar to the cam disclosed in Akers et al, U.S. Pat. No. 3,675,863. The flattened portions of the profile of FIG. 10b generate some "dwell time" at the extreme ends of the traverse by flattening of the profile. The dwell time increases the clearance of the strand guide around the pins of the pin-conveyor wheels. Accordingly the profile of FIG. 10b is preferred over the profile of FIG. 10a, which provides no dwell time at the point of traverse reversal. A further improvement in cam profile is shown in FIG. 10c, in which a small angle, α, of less than 1 degree, is created between the flattened dwell portion of the profile and the edge of the cam. This maintains a small side pressure on the yarn guide so that it smoothly enters the turn at the end of the dwell section, thereby reducing wear on the guide and permitting higher speeds.

The cam stroke must be designed so as to allow a suitable time interval at or near the end of the stroke so that the thread guide can travel beyond the position of the advancing pin on the conveyor prior to the arrival of the pin and can remain beyond the pin until after the pin has advanced through the plane of the guide's travel. This provides the wrapping of the strand onto the pin while avoiding contact between the guide and the pin. This time interval can be achieved by sufficiently extending the stroke of the cam and/or by adding an end-of-stroke dwell time to the cam profile. The end-of-stroke dwell time is preferred in that it allows a shorter overall cam stroke width to be used.

FIGS. 11a, 11b and 12 show in greater detail cam follower 38 and tip 37 of strand traverse guide 36. The cam follower is seated to slide within groove 33 of cylindrical cam 32 causing guide 36 to slide to and from between guide rails 34 and 35. In operation, as shown in FIGS. 1–6, as cylindrical cam 32 is rotated, strand traverse guide 36 moves strand 10 to and from to loop the strand about pins 42, 42' of pin-carrying conveyors 40, 40'. Pins 42, 42' are driven in a semicircular path that sweeps through the path of the strand traverse guide (after the guide has passed) to engage the strand 10. FIGS. 6 and 11a depict guide rails 34, 35 as flat. FIG. 11b depicts an upper guide rail 34, preferred for bottom-fed strand, having a shallow depression or groove in its surface at the region of closest approach of the pins 42, 42' to rail 34. This permits the pins to sweep more deeply through the strand traverse path without hitting the guide rail. Also, as shown in FIGS. 11a and 11b, for bottom fed strand, upper rail 34 is recessed by an angle θ, usually of less than 10 degrees, to further assure a close, unimpeded approach of the pins to the strand traverse path. The close approach of the pins to the face of the guide rails assures that as the pins contact the strand, the strand is secure in the notch of the traverse guide tip. Details of the notched tip of the strand guide are depicted in FIGS. 12 and 13. Such notched guide tips are disclosed by Altice et al, U.S. Pat. No. 3,086,722. If the strand is fed from above the apparatus, the central axis of the semicircular path of the pins preferably is positioned slightly below the path of strand traverse guide, and the hollows or grooved areas are on the lower guide rail to accommodate the path of the pins.

In one embodiment, tip 37 of guide 36 extends about 0.098 inch (2.5 mm) above the base of the strand guide and has a notch about 0.0602 inch (1.5-mm) deep. Of course, guides of other dimensions can be used satisfactorily. FIG. 13 illustrates a key-hole shaped notch for the tip of the strand traverse guide. The key-hole notched tip is preferred for better retention of the strand in the guide. To minimize wear and friction, tip 37 preferably is constructed of a ceramic material having a surface roughness no greater than 32 micro inches RMS. When a plastic guide is employed, the ceramic tip can be integrally molded with the plastic to form the completed guide. For higher speed operation, the weight of the traverse guide is minimized A typical plastic traverse guide with ceramic tip can weigh as little 5–10 grams.

As shown in FIGS. 1–5, strand 10, carried by reciprocating strand traverse guide 36, is looped around pins 42, 42' of a pair of pin-carrying conveyors 40, 40' to form a strand array. As illustrated in FIGS. 1–5, the pin-carrying conveyors are wheels, each having a plurality of pins projecting from its surface. A pin-carrying conveyor wheel is located near each end of the guide traverse path. The pin-conveyor wheels are spaced apart a distance that is somewhat less than the full stroke of the traverse guide. As referred to herein, the stroke of the traverse guide is equal to one-half the length of the full to-and-from traverse of the strand traverse guide. FIGS. 14a and 14b, respectively, depict a typical pin-conveyor wheel 40 with a plurality of pins 42 projecting outwardly from the wheel. The wheel has an central annular cylindrical hub 41 for mounting a drive shaft (not shown). The pins can be press-fit, brazed, welded, or bonded into spaced holes in the wheels. Typically, the wheels can be rotated at a rate in the range of 100–600 revolutions per minute at least 200 rpm is preferred.

In another embodiment of the pin wheels, the pins can be made retractable, as for example by a cam and spring mechanism, to facilitate strand removal from the pins. As illustrated in FIGS. 1 and 5 for bottom-fed strand, the axes of the pin-conveyor wheels are preferably positioned slightly above (for example, by about 2.5 mm) the elevation of the strand traverse guide path to allow deeper penetration of the pins across the path of the strand guide. As illustrated in FIG. 4 for top-fed strand, the axes of the pin-conveyor wheels are positioned slightly below the elevation of the strand traverse guide. Pin-conveyor wheels 40, 40' are driven by conventional means not shown in synchronization with the traverse guide. The pin-conveyor wheels are spaced from each other by a distance that is shorter than the traverse guide stroke but sufficiently long to permit restraining belts 52, 52' to capture the ends of the strands. The angular location of pins on the circumference of one wheel is off-set from the angular position of the pins on the circumference of the other wheel by one-half of the pin spacing. For high speed looping of strand around the pin of the pin conveyors, a minimum clearance 0.040 (1 min) between the strand traverse guide and the pins of the pin-conveyor wheels has been found to be satisfactory.

The detail drawings of FIGS. 15a and 15b, show a pin 42 canted at an angle β from the plane of wheel 40 and projecting from the surface of the pin-conveyor wheel. A typical pin can project 0.25 inch (6.4 mm) from the surface. The pin is directed slightly away from the center of the strand traverse path to improve the ability of the pin to hold the strand securely in place on the wheel. Angle β can be as large as 45 degrees, but usually is smaller. As illustrated in FIGS. 15b, the pin has a shoulder about ⅔ of the distance from the point at which the pin is secured to the wheel to the exposed end of the pin. A shoulder located between 40% and 80% of said distance usually ensures satisfactory positioning of the strand on the pin.

In FIGS. 16a and 16b, respectively, the pin-conveyor wheels 40, 40' are schematically shown to be canted toward or away from each other. Such arrangements are particularly useful with elastomeric strand. As shown in FIG. 16a, strand 10. is formed into a looped strand array on the pin-conveyor wheels, and the canted wheels allow the strand to retract before the strand is laid down on the sheet substrate carried by sheet support drum 50. In FIG. 16b, strand 10 is formed into a looped array on the pins of the pin-conveyor wheels and then stretched by the canted wheels before being laid down on the moving sheet. With this latter configuration, a shorter traverse stroke and, therefore, higher speeds can be used. While on the pins, a spandex strand typically can have an elongation that is in the range of 10 to 400% beyond its relaxed length.

As illustrated in FIGS: 1–5, sheet 12, which is to become the substrate of the composite sheet material 18 to be produced by the invention, is advanced on the surface of sheet support drum 50. Drum 50 is positioned so that at least a part of its circumferential surface is between pin-conveyor wheels 40, 40'. Other sheet support surfaces contemplated for use in supporting the sheet in its passage between the pin-conveyor wheels, include for example, an endless flat belt or screen. An endless belt is advantageous when additional time is required for maintaining the strand array and sheet assembly restrained while the adhesive is set. To keep laid-down strand array 16 in position atop advancing sheet substrate 12, a pair of restraining belts 52, 52' are employed. Restraining belt 52 is driven by contact with the moving sheet support drum around a set of four idler rolls 54, 55, 56 and 57; belt 52' is driven in the same way around corresponding idler rolls 54', 55', 56' and 57'. Idler rolls 54, 54' are positioned so that strand array 16 is initially captured at the nip between the belts going around rolls 54, 54' and rotating sheet support drum 50 before the strand looped around pins 42, 42b of pin-conveyor wheels 40, 40' is removed from the pins. Drum 50 can have circumferential grooves aligned with the restraining belts to aid the belts in holding the advancing strand array and sheet in position on the drum. Idler rolls 54, 54' preferably are of small diameter so that the distance between the point at which the strand is contacted by the restraining belts and the point at which the strand is fully captured in the nip between the belts and the drum is as small as practicable. Preferably located immediately upstream of the nips between the restraining belts and the drum, is adhesive applicator 20, which applies adhesive to the strand and/or advancing sheet. A wide variety of adhesives are suited for use in the apparatus, though hot melt spray adhesives are preferred. The width of sheet affected by the adhesive applied to the strand and/or sheet is designated "W" in FIG. 2 and is a little shorter than the distance between the restraining belts.

Figure 2:
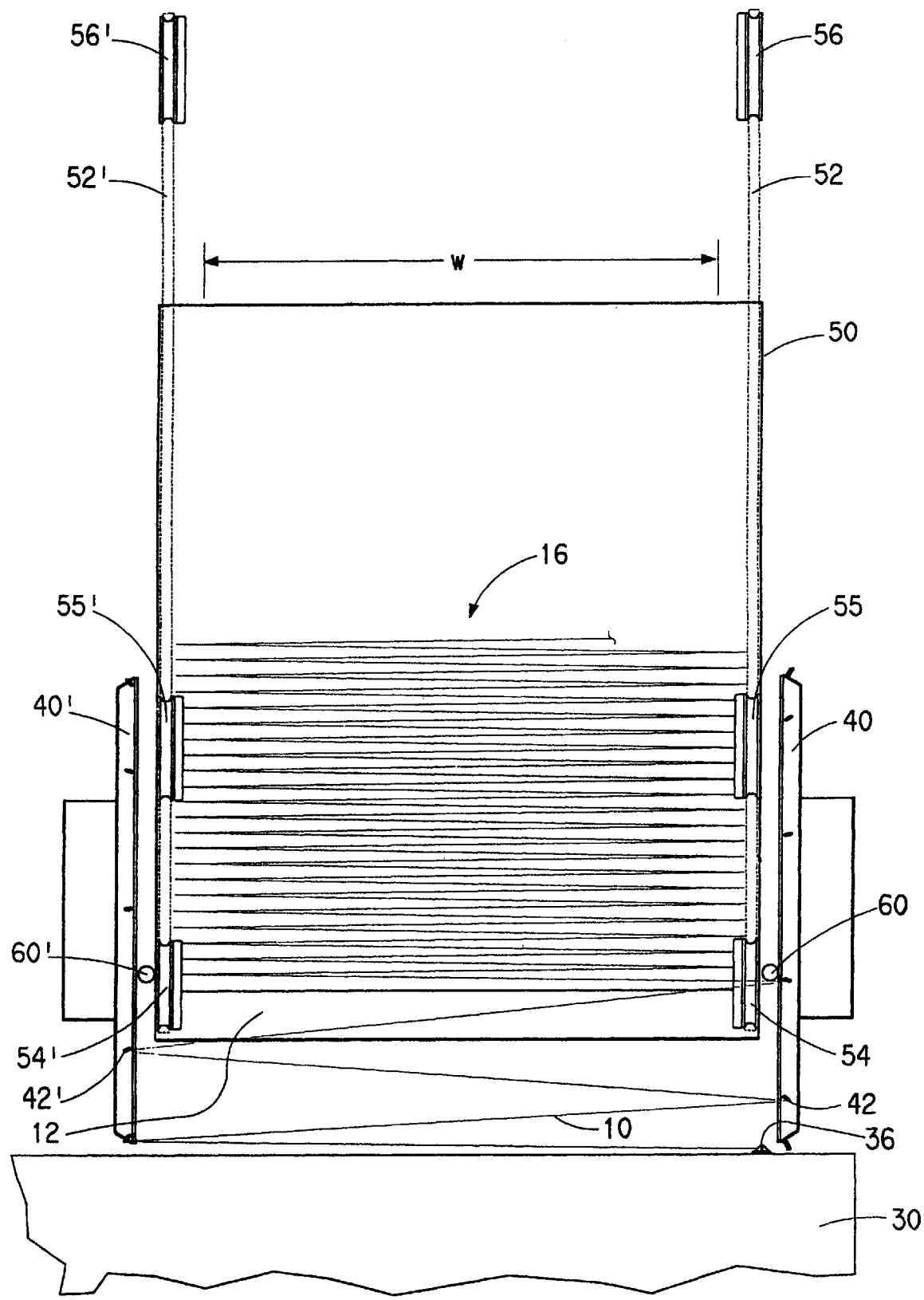
FIG. 2 is a partial top view of a portion of the apparatus of FIG. 1 showing strand 10 looped around the pins of 42, 42' of pin-conveyor wheels 40, 40', and forming a strand array 16 on support drum 50, the array being transferred atop moving sheet 12 and held in place on the drum surface by restraining belts 52, 52'.
Figure 3:
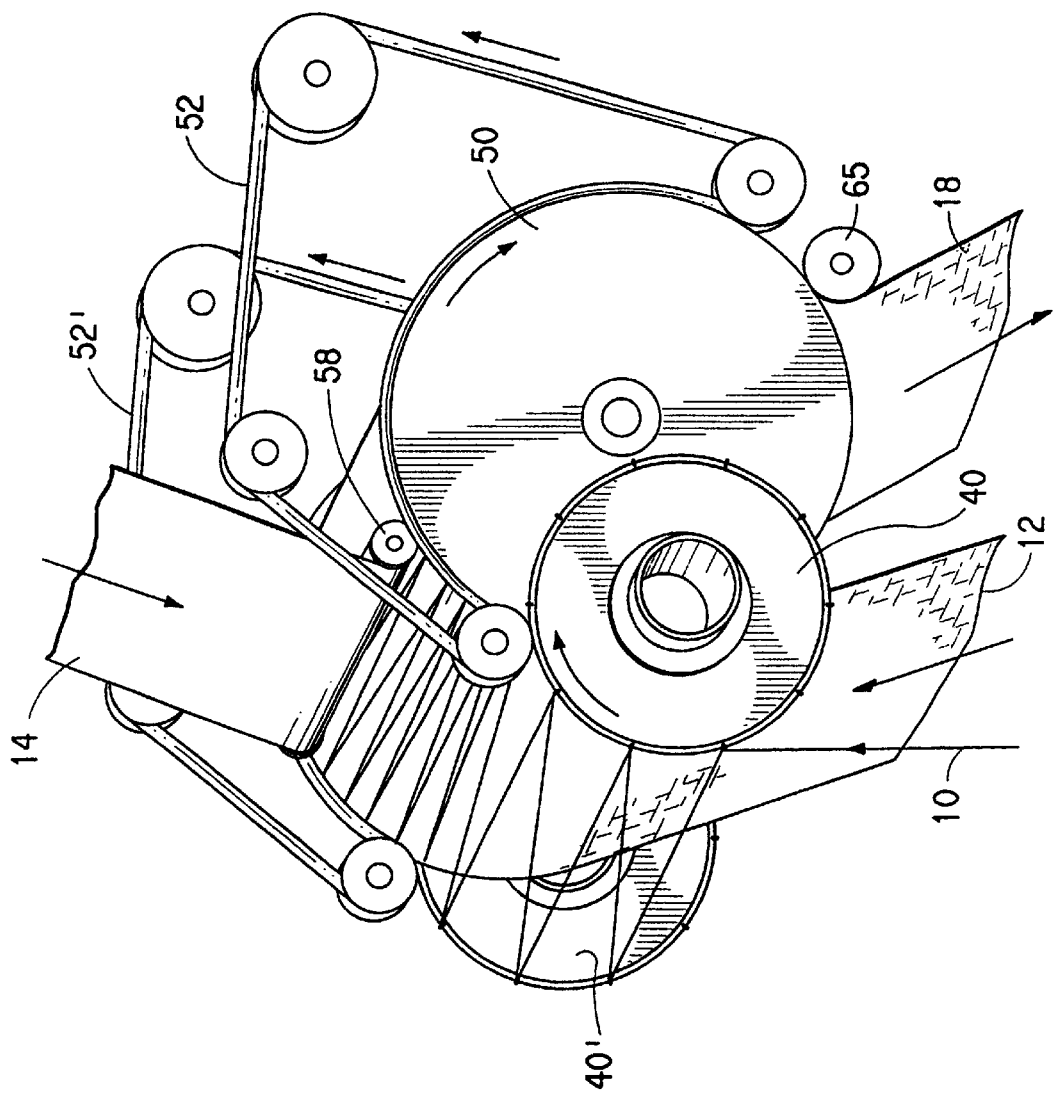
FIG. 3 is an isometric view illustrating the operation of the portion of the equipment of FIG. 1 that is located downstream of traverse guide 36.

Restraining belts 52, 52' are preferably V-belts and more preferably grooved V-belts. Such belts hold the strand and sheet on the sheet support drum more securely than do belts of round or flat cross-section. The belts are made of flexible materials to permit proper passage of the belt around the smallest diameter idler rolls (i.e., 54, 54'). Restraining belts 52, 52' operate at the same linear speed as the circumferential speed of sheet support drum 50. Immediately downstream of the just-described belt/drum nips, cutters 60, 60' are positioned on each side of drum 50 (as best illustrated in FIGS. 2 and 7). Various types of cutters can be used, such sharp edges, hot wire cutters (i.e., electrically heated resistance elements), or any other means suitable for the particular kind of strand being cut. Instead of employing cutters, stripping fingers can be positioned so as to lift the loops of strand off the pins after the strand is engaged by the restraining belts. Using stripping fingers leaves loops at the selvage of the final composite sheet product. Alternatively, folding pins can be employed to allow the loops of strand to pull free from the pins. Optionally, a press roll 58 can be used to press a cover sheet 14, supplied from roll 15, atop restrained assembly of strand array 16 and sheet substrate 12, while the assembly is still on the support drum and before the applied adhesive has set. A takeoff roll 65 can be used to guide the completed composite sheet material away from the drum and to a suitable collection means or to further processing steps. The assembly of strand, sheets and adhesive are restrained on the drum for a sufficient time (or distance on the drum) to permit the adhesive applied to the strand and sheet to set.

Figure 17A:
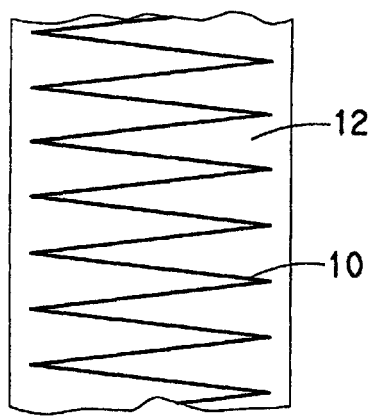
FIGS. 17a, 17b, 17c, 17d and 17e each illustrate a different strand array 16 of strand 10 applied to advancing sheet 12.
Figure 17B:
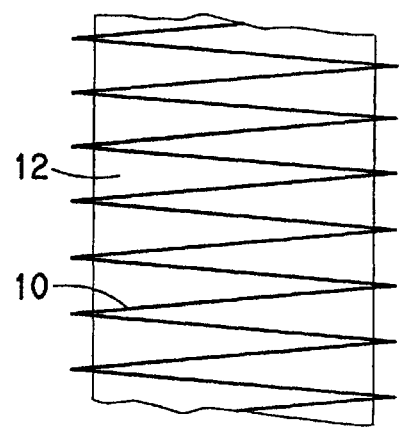
Figure 17C:
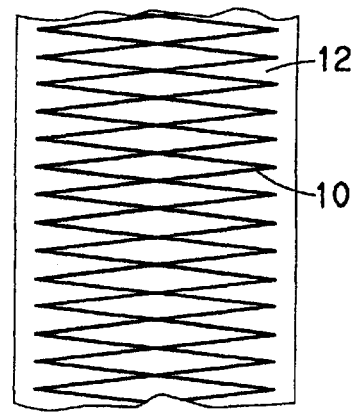
Figure 17D:
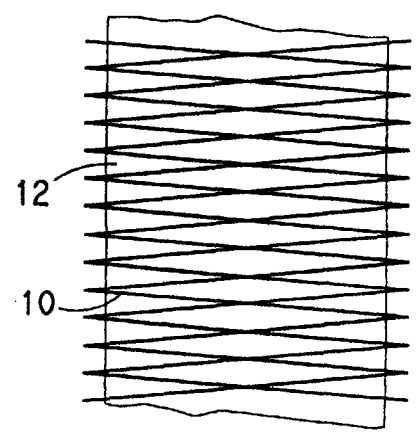
Figure 17E:
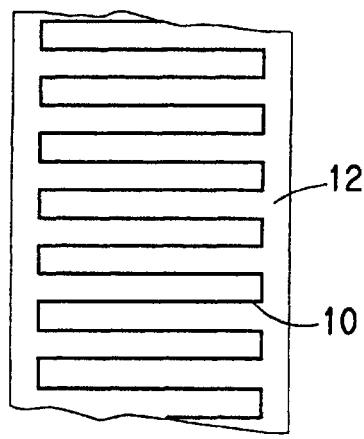

FIGS. 17a–e show various patterns of strand array 16 on substrate sheet 12 that can be made with the present invention. The array of FIG. 17a is prepared with the apparatus herein before described with regard to FIGS. 1 and 2. FIG. 17b is a similar pattern but the ends of the strand 10 extend beyond the edges of the sheet 12. This pattern can also be made if the distance between the pin-conveyor wheels is shorter than the axial length of the sheet support drum and the width of the substrate sheet. FIGS. 17c and 17d show patterns comparable to 17a and 17b, but with two strands 10 having been laid down on a sheet 12. To make these latter patterns, one pair of a pin-conveyor wheels is used in conjunction with two cam-driven strand traverse guides to loop the strands onto the pins of the pin-conveyor wheels. The pattern of FIG. 17e is made when one employs non-round (i.e., oblong) pins which rotate after having had strand looped around them. The narrow profile of the pins is presented during the strand looping. Rotation of the pins after the. strand looping "expands" the machine-direction length of the strand and results in a strand array in which the strand segments traversing the final composite sheet material are more parallel to each than when stationary pins of round cross-section are used.

The use of elastic composite sheet material of the invention is suited for installation in adult incontinence articles as waistbands, and in diapers and adult incontinence articles as stretch side panels, closure tapes, frontal tapes, back panels, leg bands, and the like. The elastic composite sheet material is also suited for installation in portions of other types of garments, such as in wrist bands of sweaters, waist bands of trousers, elastic portions of athletic sportswear.

EXAMPLE

This example describes a test that demonstrated the suitability of the process and apparatus of the invention for making elastic composite material at high speed and installing the material as elastic component in a garment, in particular an elastic waistband in disposable diapers. The apparatus for making the elastic composite sheet material used for the waistbands was substantially as illustrated in FIG. 1.

The starting materials were as follows. A 620-dtex LYCRA® XA® spandex (registered trademarks of E. I. du Pont de Nemours and Company) was used as elastic strand 10. A 23.3-g/m$^2$ Type 6700 thermally bonded polypropylene nonwoven fabric (Fiberweb Group Inc., Simpsonville, N.C.) was used as substrate sheet 12. A 0.001-inch (0.025-mm) thick polyethylene film (Consolidated Thermoplastics Co.) was used as cover sheet 14. Findley 2276 hot melt adhesive (Findley Adhesives, Inc.) was sprayed onto the strand and substrate sheet to obtain a total adhesive loading of 12 mg/in$^2$ in the final composite sheet material.

The strand was fed under tension to reciprocating strand guide which was driven by a cylindrical cam rotating at 2,000 rpm. The strand was supplied at an extension of about 300% beyond its relaxed length. The strand traverse guide had a 9.5-inch (23.5-cm) stroke and made 2,000 to-and-from cycles per minute. A pair of parallel pin-conveyor wheels, 8.75 inches (22.2 cm) apart (i.e., the minimum distance between the imaginary circles formed by the centers of the bases of the pins on each wheel) and each of 6.37 inch (16.2 cm) diameter, were rotated at 200 rpm. Each pin-conveyor wheel had ten pins equally spaced apart by a circumferential distance of 2.0 inches (5 cm). The pins were canted outward by 20 degrees from the wheel circumferential surface. The cam profile was as given in FIG. 10b. The positions of the pin wheels and strand traverse guide were set to provide a clearance of at least 0.04 inch (1 mm) between the pins and the strand traverse guide near the end of each traverse stroke. The axes of the pin-conveyor wheels were located 0.15 inch (3.8 mm) above the elevation of the axis of the path of the traverse guide. FIG. 15b illustrates the configuration that was used for the pins and the pin-conveyor wheels. Each pin was of circular cross-section and had a shoulder of the design illustrated in FIG. 15b. The pins projected above the wheel surface. The pin shoulder was located 0.07 inch (1.8 mm) from the exposed tip of the pin. The large diameter portion of the pin was 0.060 inch (1.5 mm) and the small diameter portion (i.e., the portion closest to the exposed tip of the pin) was 0.038 inch (1 mm). The sheet support drum had a 9.5 inch (23.5 cm) diameter and was rotated at 25 rpm. The resultant composite sheet material was removed from the drum at a linear velocity of about 19 meters per minute.

The composite sheet material was then fed to a commercial Nuova Red diaper-making machine which had a belt-type waistband applicator. The elastic composite sheet material was fed, cut, vacuum-transferred and glued into the disposable diapers and formed satisfactory waistbands in the diapers at a rate of about 300 diapers per minute.

What is claimed is:

1. An apparatus for making a composite sheet material including means for supplying a strand through a barrel cam and thread guide device to loop said strand around pins of a pair of spaced-apart pin conveyors and pin conveyors to transfer the strand transversely to a sheet substrate advancing in a longitudinal direction, wherein the strand guide is a reciprocating guide connected to a cylindrical cam, the strand guide having a slotted tip for receiving the strand and a follower portion for fitting a groove in the cylindrical cam, wherein the rotation of the cam drives the strand guide to and from along a traverse path having a first end and a second end wherein the pattern of the strand guide is controlled by the barrel cam design so as to allow sufficient stroke width and/or reversal dwell time to cause the strad to wrap around the pin on the advancing conveyor without striking the pin or the conveyor wherein the barrel cam has grooves, portions of which have flattened profiles which can generate dwell time at the extreme ends of the traverse path;

the cam profile and stroke width being chosen so as to allow a sufficient time interval at or near the end of each stroke to force the strand guide to remain beyond the position of the conveyor pin path to allow the strand to loop around the pin on the conveyor without striking the pin or the conveyor;

each of the pin conveyors has a plurality of evenly spaced-apart pins projecting from the surface of the conveyor, the first conveyor being positioned near the first end of the traverse path and the second conveyor being positioned near the second end of the traverse path, and the space between the conveyors being less than the distance between the first and second ends of the traverse path;

means for moving the pins of the conveyor through an arcuate path that intersects the traverse path, so that a strand carried by the reciprocating guide can loop around a pin of the pin conveyor near the end of each traverse;

a surface for supporting and advancing the sheet substrate in the longitudinal direction into a position for transferring the strand from the pins to the sheet substrate, the transfer position being located between the pin conveyors and at a nip formed by a restraining means and the support surface;

means for synchronizing the relative speeds of the reciprocating traverse guide and the pin conveyors to assure the looping of strand on a pin of the conveyor at each end of the strand path; and means for controlling the movement of the restraining means and the support surface at equal speeds.

2. The apparatus of claim 1 wherein each pin conveyor is a rotatable wheel pin conveyor; the support surface is a rotatable cylindrical drum; and the restraining means is a pair of V-belts.

3. The apparatus of claim 1 wherein the ratio of the speed of the pin conveyors and the speed of the moving sheet substrate can be varied to produce varying final cross-directional strand spacing.

4. The apparatus of claim 2 wherein the pin-conveyor wheels are canted toward each other or away from each other.

5. The apparatus of claim 1 wherein the slot of the strand guide is a key-hole slot and each pin of each pin-conveyor wheel has a shoulder located between 40% and 80% of the distance from where the pin is secured to the wheel to the top of the pin and separating a larger diameter portion of the pin from a smaller diameter portion of the pin, the smaller diameter portion being the top portion of the pin.

* * * * *